(12) United States Patent
Liu

(10) Patent No.: US 6,233,478 B1
(45) Date of Patent: May 15, 2001

(54) APPARATUS AND METHOD FOR CONSTRUCTING COMPUTED TOMOGRAPHY IMAGE SLICES OF AN OBJECT UNDERGOING CYCLIC MOTION

(75) Inventor: Pingyu Liu, Indianapolis, IN (US)

(73) Assignee: Advanced Research & Technology Institute, Bloomington, IN (US)

( * ) Notice: Subject to any disclaimer, the term of this patent is extended or adjusted under 35 U.S.C. 154(b) by 0 days.

(21) Appl. No.: 09/162,248

(22) Filed: Sep. 28, 1998

(51) Int. Cl.[7] ............................................. A61B 5/05
(52) U.S. Cl. ......................... 600/428; 600/425; 600/436; 600/437; 364/413; 364/413.13; 364/413.18; 378/8
(58) Field of Search ............................ 600/110, 407, 600/410, 425, 436, 437, 443, 444, 445, 449, 456, 481, 483, 484, 508, 509, 579, 532, 534, 428; 364/413.13, 413.18, 413; 128/653.1; 378/8

(56) References Cited

U.S. PATENT DOCUMENTS

| | | |
|---|---|---|
| 3,954,098 | 5/1976 | Dick et al. . |
| 4,182,311 * | 1/1980 | Seppi et al. ........................... 600/428 |
| 4,547,892 * | 10/1985 | Richey et al. ........................... 378/8 |
| 4,617,938 | 10/1986 | Shimoni et al. . |
| 4,868,747 * | 9/1989 | Mori et al. ........................... 382/131 |
| 4,920,413 | 4/1990 | Nakamura et al. . |
| 4,994,965 | 2/1991 | Crawford et al. . |
| 5,262,946 * | 11/1993 | Heuscher ............................... 378/15 |
| 5,280,428 * | 1/1994 | Wu et al. ......................... 364/413.13 |
| 5,383,231 | 1/1995 | Yamagishi . |
| 5,671,263 | 9/1997 | Ching-Ming . |
| 5,672,877 | 9/1997 | Liebig et al. . |
| 5,722,405 * | 3/1998 | Goldberg ............................... 600/407 |
| 5,991,356 * | 11/1999 | Horiuchi et al. ........................... 378/8 |

OTHER PUBLICATIONS

Adler, Lee P., MD, Brundage, Bruce H., MD, Shapiro, Edward, P., MD. "Tomorrow's cardiac imaging–Today" *Patient Care*. Jun. 15, 1991. pp. 143–161.

Robb, R.A., Ph.D., Morin, R.L., Ph.D. "Principles and Instrumentation for Dynamic X–Ray Computed Tomography" Ch.32, Part VI. pp. 634–668.

Ritchie, BSME, Godwin, MD, Crawford, Ph.D., Stanford, MD, Anno, MD, Kim, Ph.D. "Minimum Scan speeds for Suppression of Motion Artifacts in CT[1]" *Radiation*. Oct. 1992. pp. 37–42.

"Ultrafast Computed Tomography as a Diagnostic Modality in the Detection of Coronary Artery Disease" *Circulation*. Vo. 93, No. 5. Mar. 1, 1996. pp. 898–204.

* cited by examiner

*Primary Examiner*—Marvin M. Lateef
*Assistant Examiner*—Jeoyuh Lin
(74) *Attorney, Agent, or Firm*—Dann, Dorfman, Herrell & Skillman, P.C.

(57) ABSTRACT

Apparatus and method are provided for constructing image slices through a selected object undergoing a cyclic motion wherein a scanner is used for collecting image data associated with the selected object. A probe is provided for detecting a signal from the selected object, the signal being indicative of the cyclic motion of the object. The scanner and the probe are operatively connected with a controller. The controller receives the signal from the probe and generates therefrom a command for enabling the scanner to collect image data for producing one or more image slices through the selected object with minimized radiation exposure and data acquisition time.

36 Claims, 12 Drawing Sheets

APPARATUS AND METHOD FOR CONSTRUCTING COMPUTED TOMOGRAPHY IMAGE SLICES OF AN OBJECT UNDERGOING CYCLIC MOTION

FIELD OF THE INVENTION

The present invention relates to an apparatus and a method for radiographic imaging of a selected object and, in particular, to an apparatus and method for radiographic imaging of an object undergoing a cyclic motion.

BACKGROUND OF THE INVENTION

Imaging systems, such as computed tomography (CT) scanners, are widely used for diagnostic purposes in medical and industrial applications. However, radiographic imaging of an object is complicated when the object is not stationary. The time resolution of conventional imaging systems is typically insufficient to effectively "freeze" the motion of the object. As a result, the images produced suffer from blurring effects caused by the movement of the object. Accordingly, various techniques have been developed to enable radiographic imaging of moving objects.

One such technique has focused on the pre-alignment of a gantry associated with a computed tomography (CT) scanner. The gantry is provided to synchronously rotate a radiation source and detector. Accordingly, image data can be recorded for various source and detector positions within the rotational plane of the gantry. For the pre-alignment technique to be effective, the main motion of the object must be in one direction and the gantry must rotate in a plane perpendicular to the object's motion. Therefore, the pre-alignment technique is capable of correcting for only simple motion. Accordingly, the technique is not suitable for imaging objects, such as a beating heart, which undergo complicated motions.

Another technique, which is useful for imaging an object undergoing a cyclic motion, involves the use of retrospective gating. In that technique, a continuous stream of image data is recorded but only the data collected at the desired phase of the object is utilized. Although the retrospective gating technique may collect enough projections at the same phase of the motion for reconstruction, the data acquisition time is unpredictable and the object will be subjected to a higher radiation dose than is necessary.

A third technique for imaging a moving object requires prospective gating. In the prospective gating technique, the scanner is operated in such a way that the radiation exposure and data collection occur only when the object is at the desired phase. The prospective gating technique suffers from the same uncertainty of data acquisition time as for the retrospective gating technique.

Additionally, electron beam computed tomography systems have been developed. The time resolution of these systems is generally sufficient to record images of even rapidly moving objects, such as a beating heart. However, a high capital investment, the lack of insurance reimbursement and low image quality have prevented the acceptance of electron beam CT as a routine clinical procedure.

In light of the foregoing, it would be highly beneficial to provide an apparatus and method for producing image slices of an object undergoing cyclic motion wherein the images are essentially free from blurring effects caused by the movement of the object. Additionally, the apparatus and method should enable the image slices to be constructed on-line in a quick and robust manner. Further, the apparatus and method should minimize the object's exposure to radiation.

SUMMARY OF THE INVENTION

The problems associated with the known techniques for producing radiographic image slices of an object undergoing cyclic motion are solved to a large degree by an apparatus in accordance with the present invention. The apparatus comprises a scanner for collecting image data associated with the object, a probe for detecting a signal associated with the cyclic motion of the object, end a controller for generating a command signal which enables the scanner to collect appropriate image data such as at preselected times or at preselected phases of the cyclically-moving object.

The scanner comprises a radiation source for irradiating the object and a detector for detecting radiation from the radiation source. A gantry, having a continuously controllable speed, is provided for rotating the radiation source with respect to the selected object. The detector may be mounted on the gantry for synchronously rotating with the source or the detector may be provided as a stationary detector ring. The scanner may further comprise a bed or other support platform having a continuously controllable linear speed for supporting the object and translating the object in a selected direction relative to the scanner.

A probe is provided to detect the relative movement and/or phase of the cyclically-moving object. The controller is operatively connected to the probe for receiving a signal from the probe. The controller utilizes the probe signal to generate the command signal for enabling the scanner to collect image data for producing one or more image slices through the object at one or more selected phases of the cyclic motion. The command signal is used to control and optimize the speed of the gantry and/or the bed thereby enabling the apparatus to construct image slices through the object which are not marred by blurring effects, while subjecting the object to a minimum dose of radiation. In one embodiment, the command signal enables the scanner to operate in a single-slice mode which provides for the collection of image data at only a single predetermined phase of the cyclic motion of the selected object. In an alternate embodiment, the command signal enables the scanner to operate in a continuous mode for collecting image data of multiple image slice positions at a single phase of the motion or of a single image slice at multiple phases.

The apparatus may further comprise an image reconstructing unit for manipulating the image data to construct image slices through the selected object. The image reconstructing unit comprises a reordering unit for generating reordered image data. Since the image data is not necessarily collected in the proper order for image reconstruction, the reordering unit organizes the data to create a complete data section. The reconstructing unit further comprises a rebinning unit for generating parallel beam data from the reordered image data. The rebinning unit converts the reordered fan beam data to parallel beam data using formulas that relate fan beam parameters to corresponding parallel beam parameters. An image slice reconstructing unit is provided for constructing an image slice of a specific phase of the object from the parallel beam data.

In another of its aspects, the present invention relates to a method for constructing image slices through an object undergoing a cyclic motion. The method comprises the steps of generating an average period of the cyclic motion from a signal derived from the object. A window width is then selected to be less than a predetermined portion of the average period of the cyclic motion. When a single slice of a selected phase is desired, the window width represents the time that the radiation source is turned on for each cyclic motion period. When multiple slices are to be reconstructed, the radiation source is turned on for a consecutive time period and the window width is instead used for selecting proper sections of the data to reconstruct image slices with a desired phase.

A gantry rotation period is generated from the average period of the cyclic motion and the window width. The average period of the cyclic motion, the window width, and the gantry rotation period are then used to determine a minimum number of cyclic motion periods required to obtain a complete set of data. Then, a sampling period is generated from the gantry rotation period and the number of source beams in a complete gantry rotation. Additionally, when a single image slice at a selected phase is to be constructed, a time delay for a selected phase condition is generated from the average period. The time delay insures that the object will be in the desired place when image data is collected. Therefore, a series of images may be acquired of the object while in the same phase of motion.

When image slices at multiple positions are to be constructed, the average period, the gantry rotation period, and the minimum number of cyclic motion periods are utilized to determine a bed advance speed. The average period of the cyclic motion, the window width, the gantry rotation period, the minimum number of cyclic motions required to obtain a complete set of data, the sampling period, the time delay, and the bed advance speed are then transmitted to the scanner for collecting image data associated with the object. Image data associated with the object is then recorded and reconstructed to generate an image slice of the object.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figure 1:
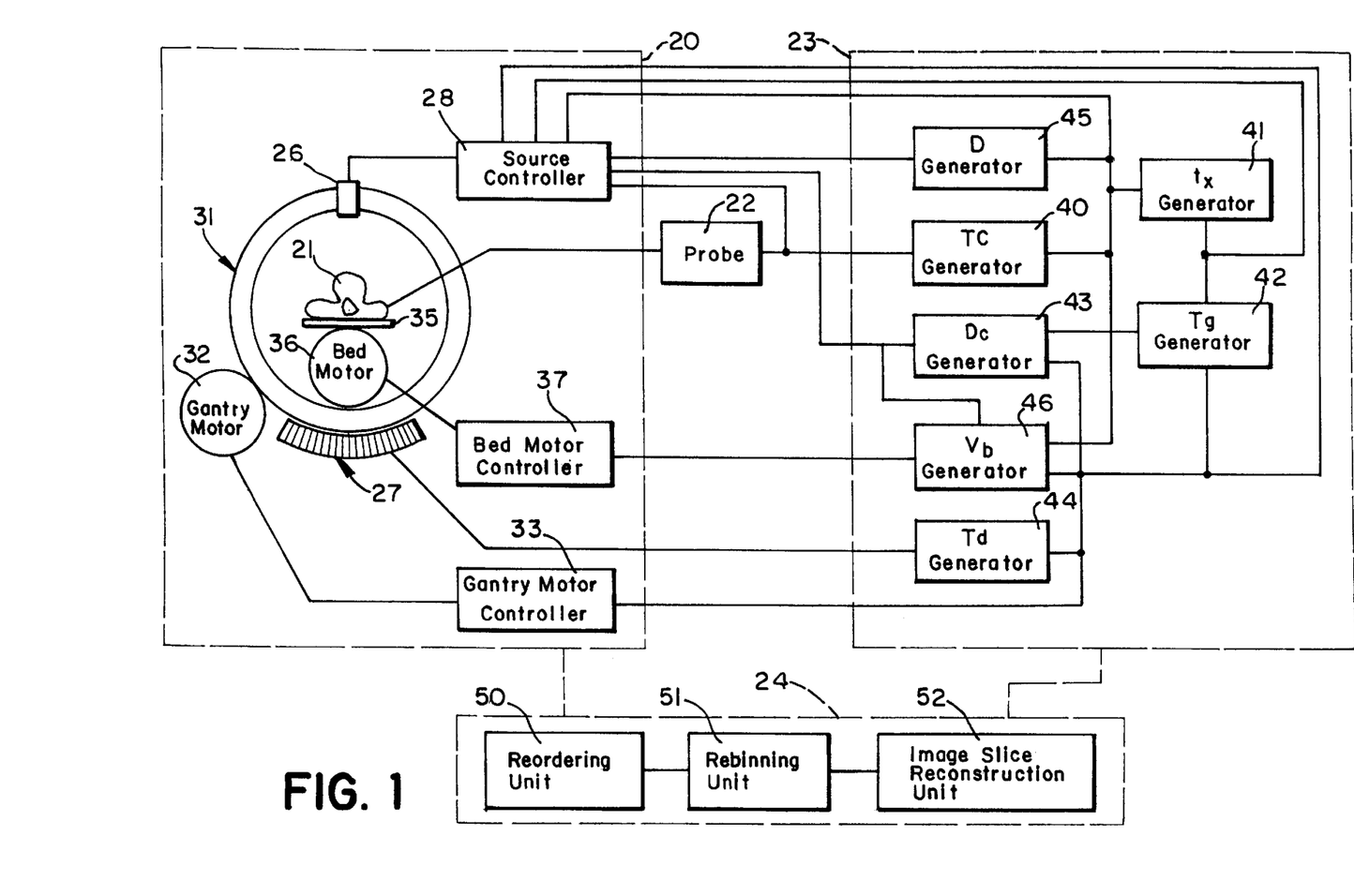
FIG. 1 is a schematic view of an apparatus for constructing an image slice through a selected object in accordance with the present invention.

An apparatus in accordance with the present invention is depicted schematically in FIG. 1. The apparatus comprises a scanner 20, such as a CT scanner, for generating image data associated with a selected object 21 and a probe 22 for detecting relative movement or phase of the object. In response to the selected object's movement, the probe produces a signal associated with movement, such as a cyclic motion, of the selected object. A controller 23 is connected to both the scanner 20 and the probe 22. The controller 23 utilizes the probe signal identifying relative movement or phase of the object to produce a command signal for control of the scanner 20. The command signal invokes the scanner 20 to selectively collect image data for a single image slice at a predetermined phase of the cyclic motion of the selected object 21, for a single image slice at multiple phases, or for multiple image slices at a predetermined phase. The apparatus may further comprise an image reconstruction unit 24 for generating one or more tomographic images of the selected object 21 from the image data.

The scanner 20 comprises a radiation source 26 for irradiating the selected object 21 and a detector 27 for detecting radiation from the radiation source 26. A radiation source controller 28 is provided to regulate the collection of image data by the source 26 and the detector 27. For example, the scanner 20 may be a conventional X-ray computed tomography (CT) imaging system. The radiation source 26 may consist of a single radiation source or a plurality of individual radiation sources. The detector 27 may be either one or two dimensional and either fixed or rotational.

The scanner 20 further comprises a gantry 31, a gantry motor 32, and a gantry motor controller 33 for accurately controlling the motion of the radiation source 26 and detector 27 with respect to the selected object 21. In order to minimize the data acquisition time and motion artifacts within the image data, the speed of the gantry 31 is continuously controllable.

The scanner 20 may be utilized to construct a single image slice of a selected phase of the cyclic motion, a single image slice at any phase of the multiple phases associated with the cyclic motion, or a continuous series of image slices at a desired phase. When a single image slice of a selected phase is desired, exposure to radiation from the source 26, as well as the corresponding data acquisition, is performed with uniform gating at the selected phase of the cyclic motion. In other words, image data is acquired only when the object is detected to be in the desired phase. However, when a single image slice of multiple phases or a continuous linear series of image slices of a single phase are desired, the exposure and data acquisition is conducted continuously.

To acquire image data for a single slice for multiple phases, images are acquired at different phases of cyclical movement of the object but while the object is maintained at the same linear slice position. When the scanner 20 is to be operated in a continuous mode to collect image data for multiple image slice positions through the selected object 21, the scanner 20 also comprises a bed 35 or other support platform for supporting and translating the selected object 21 in a selected linear direction through the source-detector axis. A bed motor 36 and bed motor controller 37 are used to regulate the movement of the bed 35. Similar to the gantry 31, the bed speed is continuously controllable in order to minimize both the data acquisition time and motion artifacts.

The probe 22 comprises a transducer for detecting relative movement of the object and for providing a signal associated with such motion of the selected object. For example, the probe 22 may comprise an electrocardiograph for monitoring a beating heart to produce an electrocardiogram.

The controller 23 is connected with the probe 22 to receive the signal from the probe 22. In response to the probe signal, the controller 23 generates a command signal for enabling the scanner 20 to selectively collect image data associated with the selected object 21. The command signal generated by the controller 23 enables the scanner 20 to collect image data for producing one or more image slices through the selected object 21 at one or more selected phases of the cyclic motion. The command signal functions to optimize the speed of the gantry 31 and/or the speed of the bed 35 of the scanner 20, as well as to synchronize the collection of data with the movement of the gantry 31 and the bed 35. Accordingly, the controller 23 is operatively connected to the gantry motor controller 33, the bed motor controller 37, and the radiation source controller 28. In one embodiment, the command signal enables the scanner 20 to collect image data only at a single predetermined phase of the cyclic motion of the selected object. In another embodiment, the command signal enables the scanner to collect image data a different or multiple phases of the cyclic motion, as discussed below.

The controller 23 comprises a series of generators, 40–46, for generating an average period of the cyclic motion ($T_c$), a window width ($t_x$), a gantry rotation period ($T_g$), a minimum number of cyclic motion periods required to obtain a complete set of data ($n_c$), a sampling period ($T_d$), a time delay (D), and a bed advance speed ($V_b$), respectively. The $T_c$ generator 40 is connected to the probe 22 for receiving the signal from the probe 22 and generating the average period of the cyclic motion. The $T_c$ generator 40 is also connected with the $t_x$, $T_g$, $n_c$, D, and $V_b$ generators, 41, 42, 43, 45, and 46, respectively, to transmit the average period of the cyclic motion to each of those generators. In addition, the $T_c$ generator 40 is connected with the source controller 28 to supply the average period of the cyclic motion to the source controller 28.

The $t_x$ generator 41 receives the average period of the cyclic motion from the $T_c$ generator 40 and generates therefrom a window width that defines the length of time that the source is on or, alternatively, represents a selected segment of data corresponding to a selected phase when data is continuously acquired. The $t_x$ generator 41 is connected to the $T_g$ generator 42 for supplying the window width to the $T_g$ generator 42. In addition, the $t_x$ generator 41 is connected to the source controller 28 for supplying the window width to the source controller 28.

The $T_g$ generator 42 receives the average period of the cyclic motion from the $T_c$ generator 40 and the window width from the $t_x$ generator 41. In response, the $T_g$ generator 42 generates the gantry rotation period and transmits the gantry rotation period to the $n_c$, $T_d$, and $V_b$ generators, 43, 44 and 46, respectively. The $T_g$ generator 42 is also connected to the gantry motor controller 33 for transmitting the gantry rotation period to the controller 33.

The $n_c$ generator 43 receives the average period of the cyclic motion from the $T_c$ generator 40 and the gantry rotation period from the $T_g$ generator 42. In response, the $n_c$ generator 43 generates the minimum number of cyclic motion periods required to obtain a complete set of data. The $n_c$ generator is also connected to the $V_b$ generator 46 and the source controller 28 for transmitting the minimum number of cyclic motion periods required to obtain a complete set of data to the $V_b$ generator 46 and the controller 28.

The $T_d$ generator 44 receives the gantry rotation period from the $T_g$ generator 42 and generates therefrom a sampling period for the source to activate. The $T_d$ generator is connected to the detector 27 for supplying the sampling period to the detector 27.

The D generator 45 receives the average period of the cyclic motion from the $T_c$ generator 40 and generates therefrom a time delay that represents the desired time from the start of the cyclic motion to provide the desired phase of the cyclic motion. The D generator 45 is connected to the source controller 28 for transmitting the time delay to the controller 28.

The $V_b$ generator 46 receives the average period of the cyclic motion from the $T_c$ generator 40, the gantry rotation period from the $T_g$ generator 42, and the minimum number of cyclic motion periods required to obtain a complete set of data from the $n_c$ generator 43. In turn, the $V_b$ generator 46 generates the bed advance speed and transmits the bed advance speed to the bed control motor 37.

The image reconstruction unit 24 is connected to the scanner 20 and the controller 23 to produce desired image slices from the acquired image data. The image reconstruction unit 24 receives initial and final gantry positions, as well as the image data, from the scanner. In addition, the image reconstruction unit 24 receives from the controller 23, the sampling period, the bed advance speed, the time delay, the minimum number of cyclic motion periods required to obtain a complete set of data, the window width, and the gantry rotation period. The image reconstruction unit 24 comprises a reordering unit 50 for generating reordered image data. The reordering unit 50 receives the image data from the scanner 20 and reorders the image data from different cycles in a proper order. For example, when $T_g < T_c$, the reordering module stores data in a forward sequential order, i.e., the image data measured for the second cyclic motion period follows immediately after the image data measured for the first cyclic motion period, and so on for the data measured for each of the cyclic motion periods. For cases of $T_g > T_c$, the reordering module stores data in a backward sequential order, i.e., the image data measured for the second cyclic motion period will be put in front of the image data measured for the first cyclic motion period, and so on. A rebinning unit 51 utilizes the reordered image data to generate parallel beam data using formulas to relate fan beam parameters from the acquired data to corresponding parallel beam parameters. An image slice of a specific phase of the selected object 21 is then constructed from the parallel beam data by an image slice reconstructing unit 52. The image slice reconstructing unit 52 creates an image slice using a filtered backprojection method.

In operation, the apparatus of FIG. 1 is utilized in a method for constructing one or more image slices through a selected object undergoing a cyclic motion. The steps of the method are depicted in the flow chart of FIG. 2. At step 70, a signal associated with the cyclic motion of the selected object is monitored.

Figure 2:
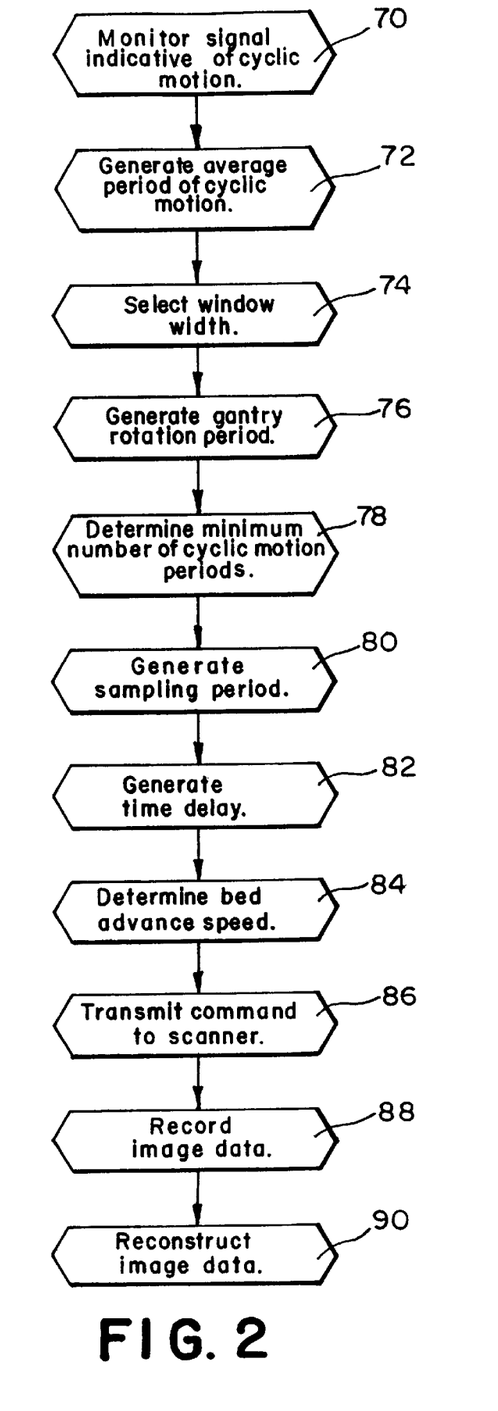
FIG. 2 is a flow chart depicting the steps of a method for constructing an image slice through a selected object in accordance with the present invention.
Figure 3:
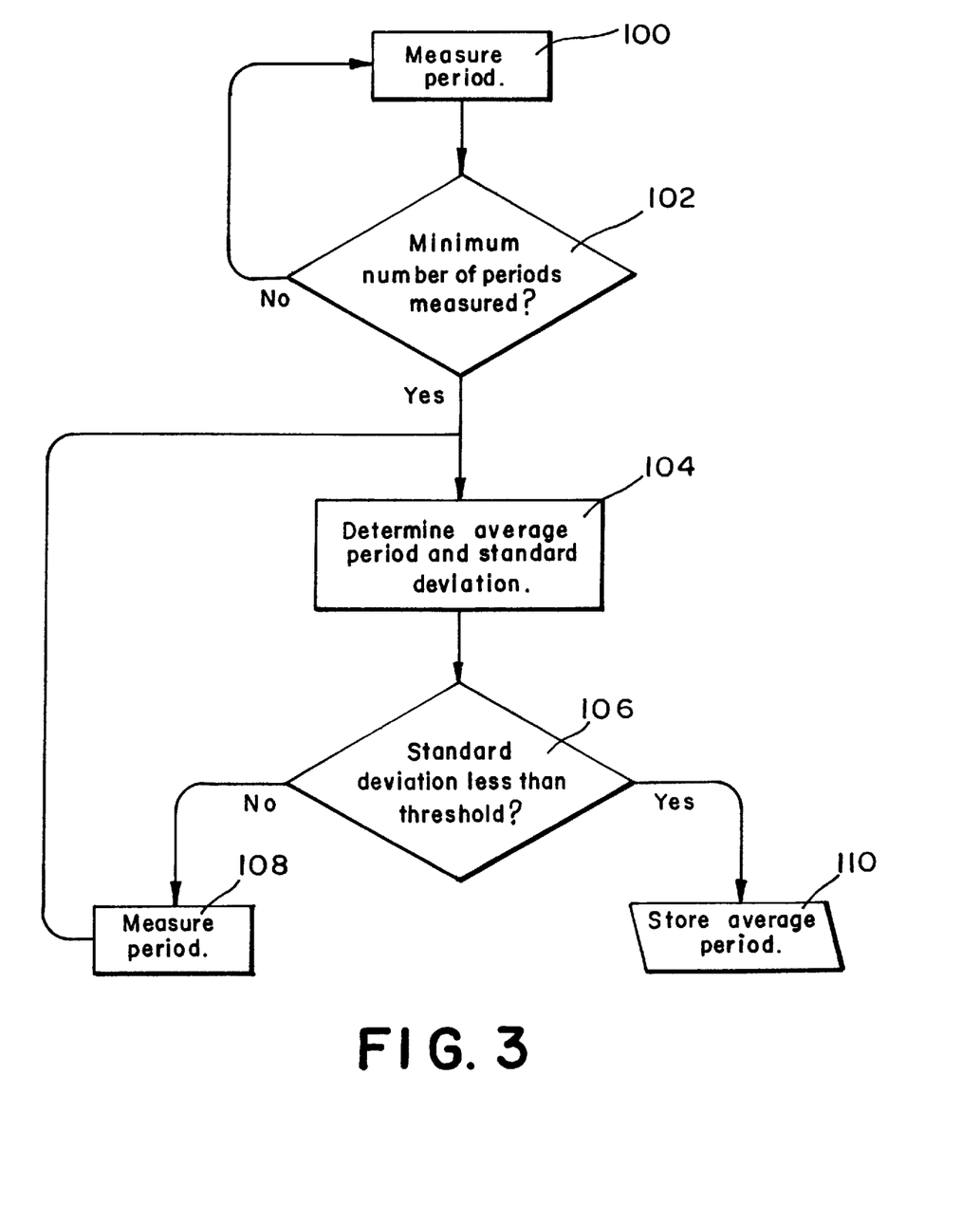
FIG. 3 is a flow chart depicting the steps of a method for generating an average period of a cyclic motion associated with a selected object.

The average period of the cyclic motion is generated at step 72 from the signal derived from the selected object. Referring to FIG. 3, an individual period of the cyclic motion is measured at step 100. At step 102, it is determined whether the number of periods measured equals a selected minimum number of periods. The minimum number of periods is selected to represent the number of periods generally necessary to obtain a statistical sampling. If the number of periods measured equals the minimum number of periods, the average period and standard deviation associated with the average period are determined at step 104.

If, however, the number of periods measured is less than the minimum number of periods, additional periods are measured at step 100 until the number of periods measured equals the minimum number of periods. When the number of periods measured equals the minimum number of periods the average period and standard deviation are determined at step 104.

Once the average period and standard deviation have been determined, the standard deviation is compared to a threshold value at step 106. The threshold value represents a clinically tolerable spread in the measured periods. If the standard deviation is less than the threshold value, then the average period is stored at step 110. However, if the standard deviation is greater than the threshold value, an additional period is measured at step 108 and, the average period and standard deviation recalculated at step 104 and compared to the threshold value at step 106.

Figure 9:
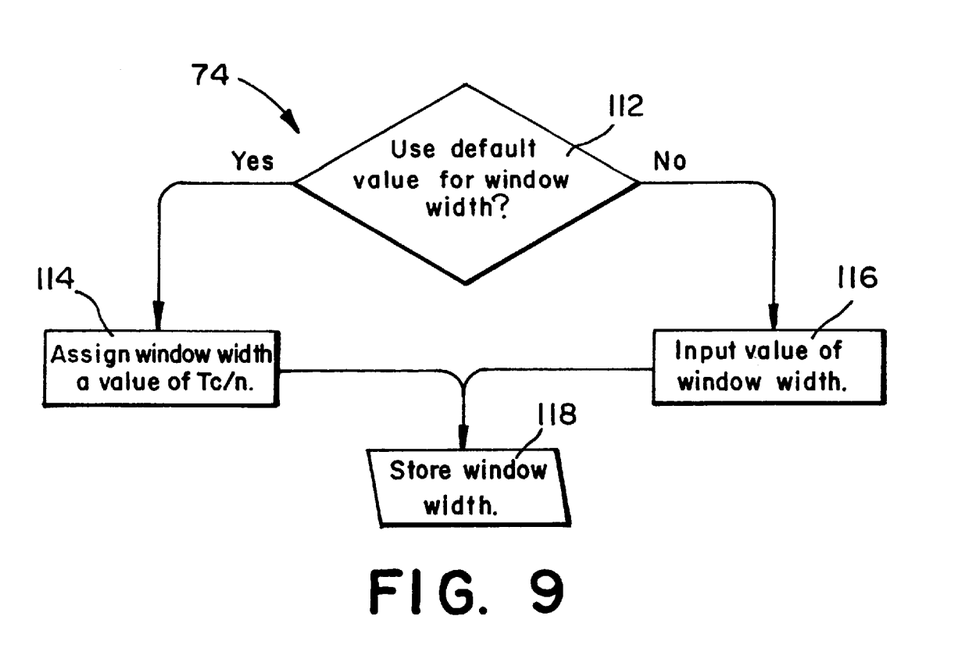
FIG. 9 is a flow chart depicting the steps of a method for selecting a window width.

Returning to FIG. 2, the window width is selected at step 74. When a single slice of a selected phase is desired, the window width represents the time that the radiation source is turned on for each cyclic motion period. When multiple slices are to be reconstructed, the radiation source is turned on for a consecutive time period and the window width is instead used for selecting proper sections of the data to reconstruct image slices with a desired phase, as if the radiation source were turned on only for the desired phase. Referring to FIG. 9, the window width is selected by first determining whether a default value for the window width will be used at step 112. If the default value of the window width is to be used, the default value is determined, based on the experience of typical operators and the specific object being imaged, at step 114. In one embodiment, the default window width is a fractional part of the cyclic motion, for example $t_x = T_c/n$ where "n" is a number greater than 3. If the default value of the window width is not being used, the operator inputs a value for the window width at step 116. The window width should be selected based upon the operator's own experience. Generally, the window width must be sufficiently short to acquire data during a time period wherein the object being imaged does not move appreciably. However, if the window width is too short, the data acquisition time will be undesirably long. The value of the window width is then stored at step 118.

Referring again to FIG. 2, the gantry rotation period is generated at step 76 from the average period of the cyclic motion and the window width. By design, all scanners will have an associated minimal gantry rotation period, $T_{g0}$, and therefore, $T_g$ must be greater than $T_{g0}$. Further, to minimize data acquisition time, the gantry rotation period should be either the sum or the difference between the cyclic motion period, $T_c$, and the window width, $t_x$. Since the shortest gantry rotation period is desired to minimize blurring effects caused by the cyclic motion of the selected object, the gantry rotation period should be set to the difference between the cyclic motion period and the window width whenever that difference is greater than the minimal gantry rotation period.

Figure 4:
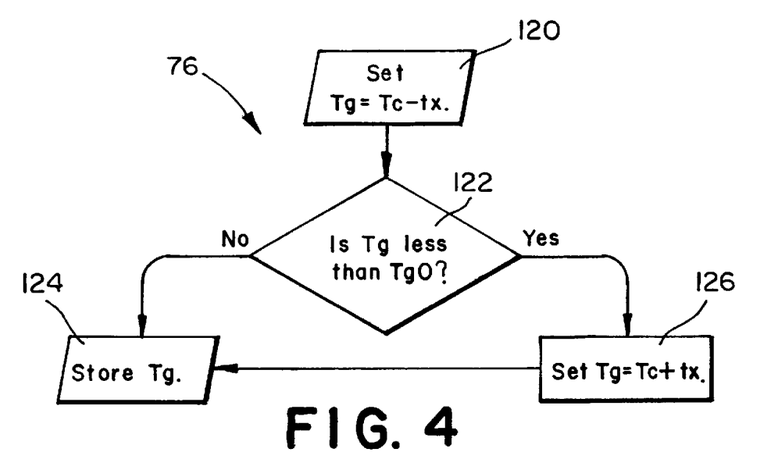
FIG. 4 is a flow chart depicting the steps of a method for generating a gantry rotation period.

The foregoing considerations are accounted for in the steps depicted in FIG. 4 for generating the gantry rotation period. At step 120, the gantry rotation period $T_g$ is set to the difference between the average period $T_c$ and the window width. The gantry rotation period $T_g$ is compared to the minimal gantry rotation period $T_{g0}$ at step 122. If the gantry rotation period is not less than the minimal rotation period, the gantry rotation period is stored at step 124. However, if the gantry rotation period is less than the minimal rotation period, the gantry rotation period is set to the sum of the average period and the window width at step 126 and the gantry rotation period is stored at step 124.

Figure 5:
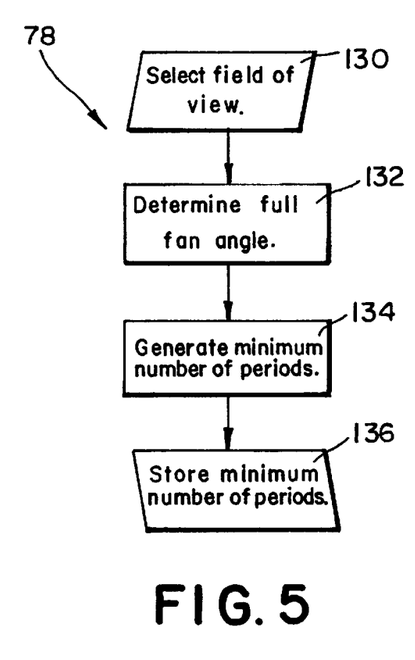
FIG. 5 is a flow chart depicting the steps of a method for generating a minimum number of cyclic motion periods required to obtain a complete set of data.

With reference again to FIG. 2, the minimum number of cyclic motion periods required to obtain a complete set of data is determined, at step 78, from the average period of the cyclic motion, the window width, and the gantry rotation period. Referring to FIG. 5, a field of view is selected, at step 130, based on the size of the object being imaged. A full fan angle, $\phi_f$, is determined from the field of view at step 132 by dividing the field of view by the distance from the source to the rotation center. The minimum number of cyclic motion periods is then generated as $$n_c = \frac{(180° + \phi_f)}{360°} \frac{T_g}{t_x}$$

at step 134 and stored at step 136.

Figure 6:
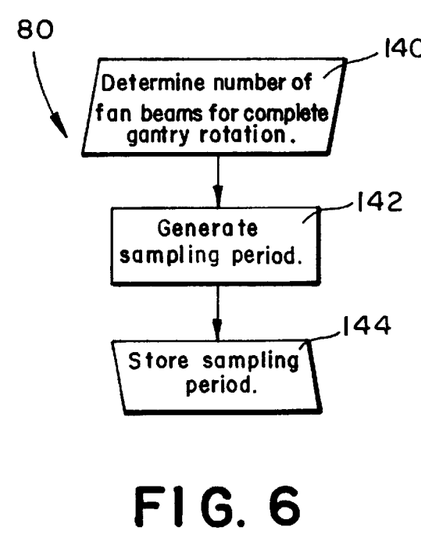
FIG. 6 is a flow chart depicting the steps of a method for generating a sampling period.

Returning to FIG. 2, the sampling period is generated at step 80 from the gantry rotation period, $T_g$, and a number of source beams in a complete gantry rotation, $N_x$. The gantry rotation period will affect the data acquisition sampling period. Specifically, each detector has to be sampled with a period, $T_d$, equal to $T_g/N_x$. The steps involved in generating the sampling period are depicted in FIG. 6. At step 140, the number of fan beams taken for a complete gantry rotation is determined from the required transverse spatial resolution of reconstructed images. The value of the sampling period is then generated as $T_g/N_x$ at step 142 and stored at step 144.

Figure 7:
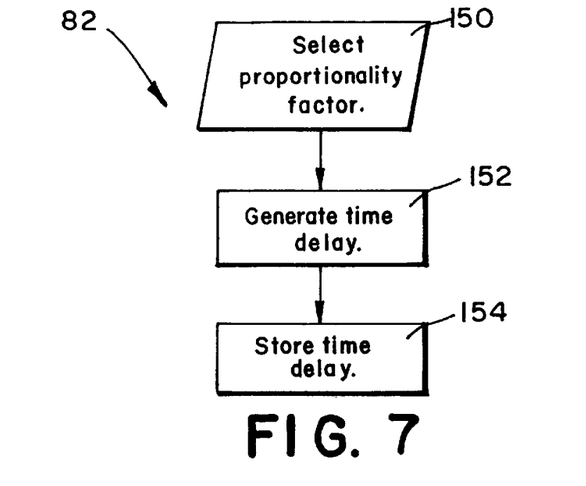
FIG. 7 is a flow chart depicting the steps of a method for generating a time delay for a selected phase condition.

Referring again to FIG. 2, the time delay for a selected phase condition is generated from the average period of the cyclic motion at step 82. When a single slice at a selected phase is desired, the time delay must be generated in order to insure that the radiation source is turned on at the selected phase for each cyclic motion. Referring to FIG. 7, the time delay is generated by selecting a delay factor, $\alpha$, at step 150. The time delay is then generated as the product of the delay factor and the average period of the cyclic motion at step 152 and stored at step 154.

Figure 8:
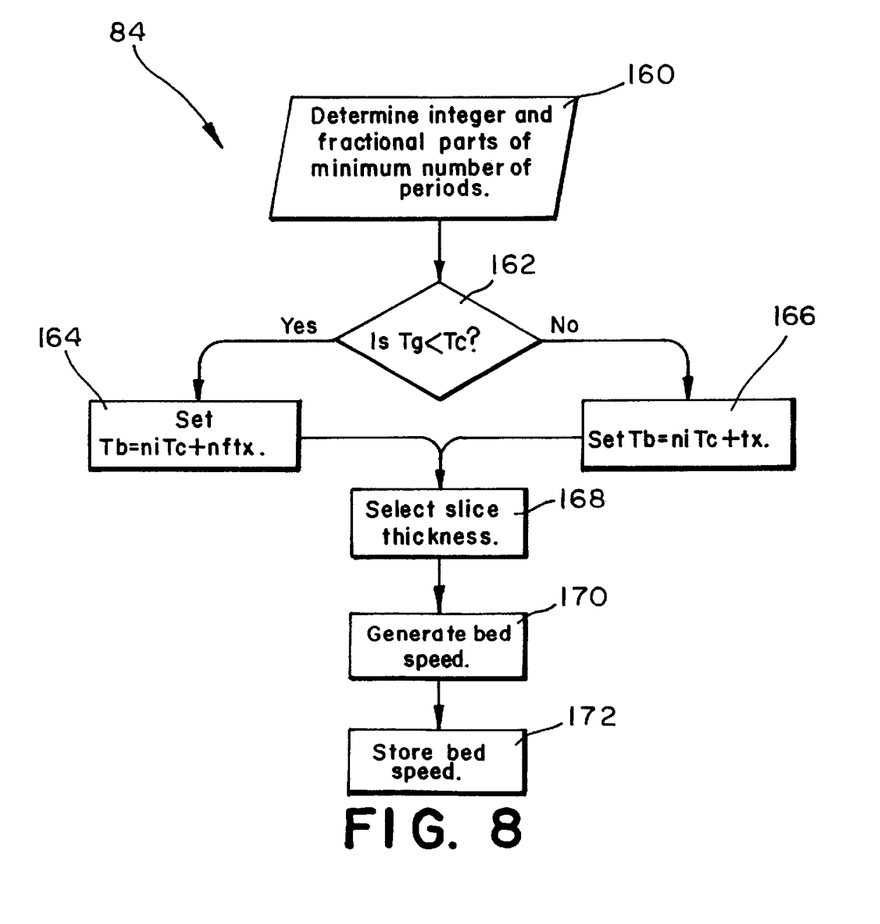
FIG. 8 is a flow chart depicting the steps of a method for determining a bed advance speed.

When image data for multiple slice positions through the selected object are to be collected (i.e., the continuous data collection mode), the bed advance speed, $V_b$, is determined at step 84 of FIG. 2. The bed advance speed is determined from the average period of the cyclic motion, the gantry rotation period, and the minimum number of cyclic motion periods required to obtain a complete set of data. Specifically, the bed advance speed is generated by determining a slice time, $T_b$, corresponding to the time required for the bed to move a preselected slice thickness, d. The bed advance speed is then generated using the preselected slice thickness and the slice time. Referring to FIG. 8, the integer and fractional parts, $n_i$ and $n_f$ respectively, of the minimum number of cyclic motion periods required to obtain a complete set of data, $n_c$, are determined at step 160. For example if $n_c$=2.7, then $n_i$=2 and $n_f$=0.7. The gantry rotation period $T_g$ is compared to the average period of the cyclic motion $T_c$ at step 162. If the gantry rotation period is less than the average period of the cyclic motion, the slice time, $T_b$, is set to $n_i T_c + n_f t_x$ at step 164. However, if the gantry rotation period is not less than the average period of the cyclic motion, the slice time is set to $n_i T_c + t_x$ at step 166. The slice thickness is then chosen at step 168 from the required longitudinal spatial resolution of reconstructed images. The bed advance speed is then generated as the slice thickness divided by the slice time at step 170 and stored at step 172.

At step 86 of FIG. 2, the commands for control of the scanner are transmitted to the scanner. Specifically, the average period of the cyclic motion, the window width, the gantry rotation period, the minimum number of cyclic motion periods required to obtain a complete set of data, and the time delay are transmitted to the source controller of the scanner. Likewise, the bed advance speed is transmitted to the bed motor controller, the sampling period is transmitted to the detector, and the gantry rotation period is transmitted to the gantry motor controller. The transmitted commands are used to control the scanner and record image data at step 88.

Figure 10:
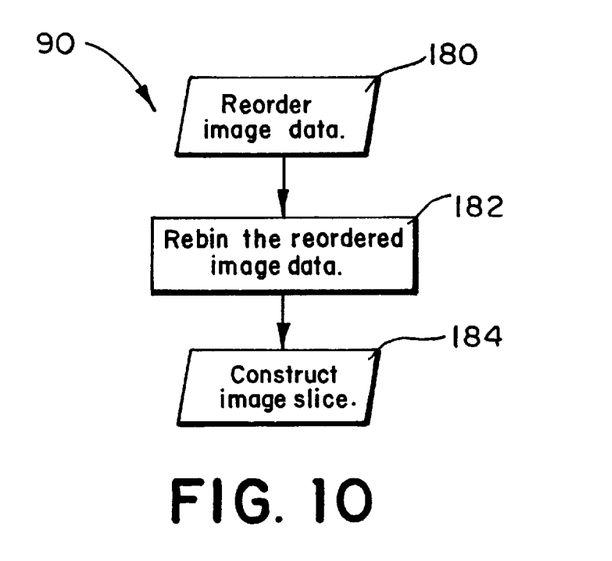
FIG. 10 is a flow chart depicting the steps of a method for reconstructing image data to generate an image slice of a selected object.

At step 90, the image data is reconstructed to generate one or more image slices of the selected object. The steps involved in reconstructing the image are depicted in FIG. 10. The image data is reordered to generate reordered image data at step 180 by organizing the image data to be in a proper order. The reordered image data is then rebinned at step 182 to generate parallel beam data. At step 184, an image slice of a specific phase of the selected object is constructed from the parallel beam data.

Figure 11:
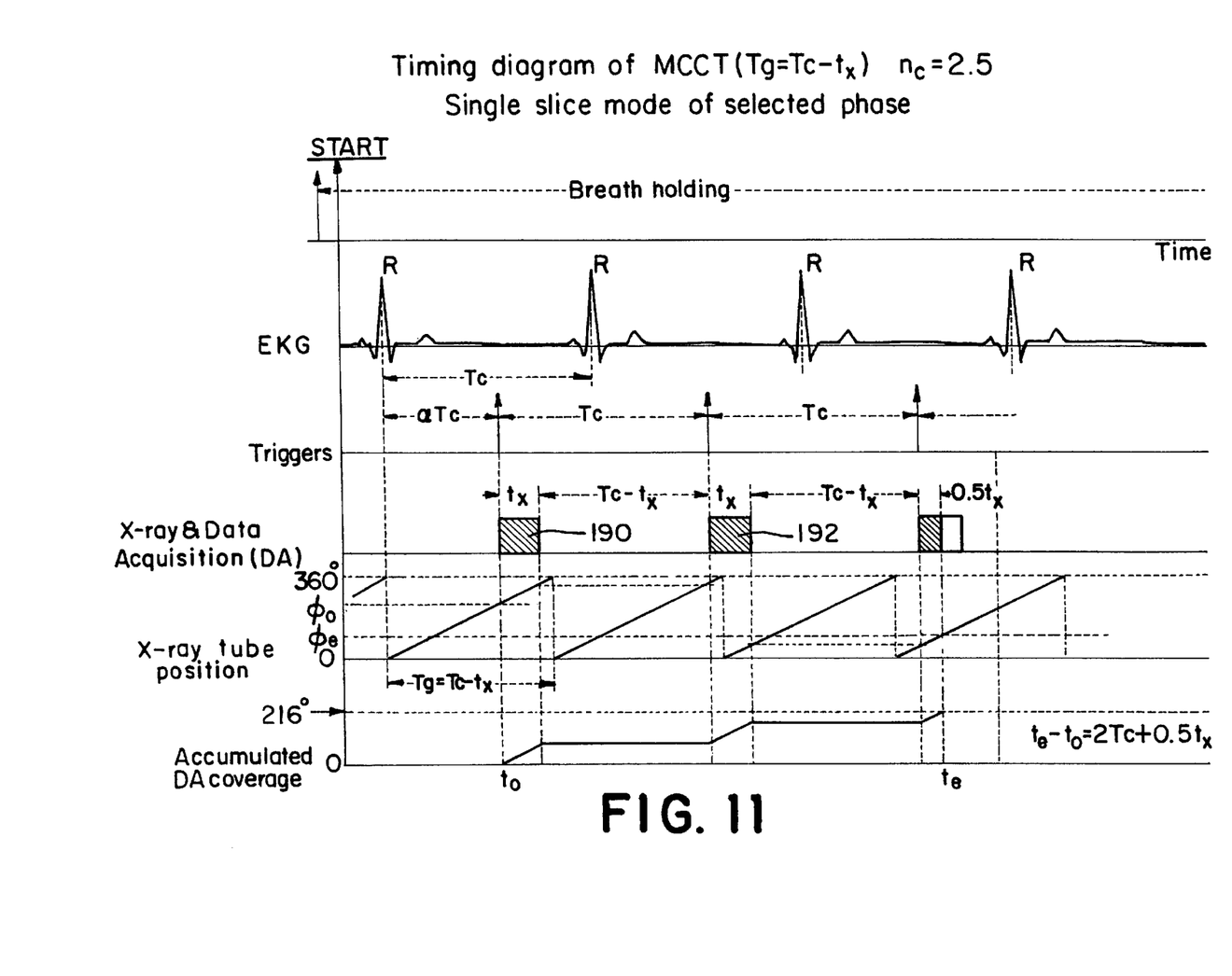
FIG. 11 is a schematic view of a timing diagram for generating a single image slice through a selected object at a selected phase when the gantry rotation period is the difference between the average period and the window width.
Figure 12:
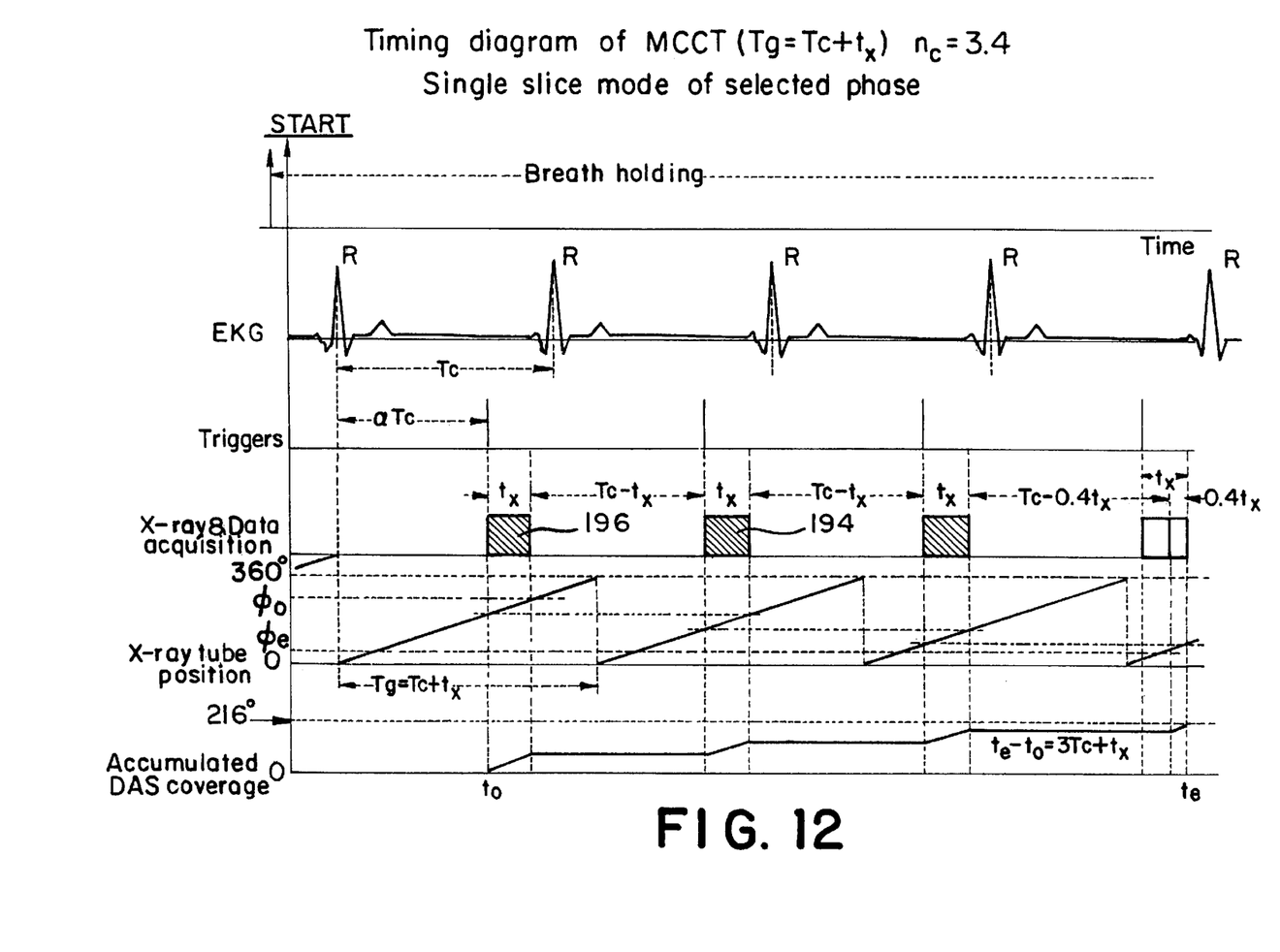
FIG. 12 is a schematic view of a timing diagram for generating a single image slice through a selected object at a selected phase when the gantry rotation period is the sum of the average period and the window width.

When a single image slice of a selected phase is to be constructed, the reordering module stores the original fan beam data in a special order to make a complete data section for reconstruction. For cases of $T_g < T_c$, the reordering module stores data in a forward sequential order, i.e., the image data measured for the second cyclic motion period follows immediately after the image data measured for the first cyclic motion period, and so on for the data measured for each of the cyclic motion periods. Referring to FIG. 11, it can be seen that the x-ray tube position at the end of the first image data acquisition period 190 is the same as the x-ray tube position at the start of the second image data acquisition period 192. Therefore, arranging the image data in sequential order requires the second image data to follow the first image data. For cases of $T_g > T_c$, the reordering module stores data in a backward sequential order, i.e., the image data measured for the second cyclic motion period will be put in front of the image data measured for the first cyclic motion period, and so on. Referring to FIG. 12, it can be seen that the x-ray tube position at the end of the second image data acquisition period 194 is the same as the x-ray tube position at the start of the first image data acquisition period 196. Therefore, arranging the image data in sequential order requires the first image data to follow the second image data. This reordering procedure will be performed on all $n_c$ cyclic motion periods to make a contiguous image data section.

The rebinning module then converts the reordered fan beam data to generate parallel beam data using formulas relating fan beam parameters to corresponding parallel beam parameters. The reconstruction module constructs the image slice, using the rebinned and reordered contiguous parallel beam data, using a filtered back projection method. The initial and ending angular positions of the gantry, $\phi_0$ and $\phi_e$, are used to correct the orientation of the reconstructed image to a desired angle.

The image reconstruction procedure for the single slice mode of any phase or the continuous mode requires that the desired cyclic motion phase be chosen. Once chosen, the image slice or slices are constructed as described above with reference to the single image slice of a selected phase.

Examples of the application of the method in accordance with the present invention to a series of common clinical situations are depicted in FIGS. 11–16. In the examples of FIGS. 11–16, a patient's beating heart is monitored using an electrocardiogram (EKG). The resulting electrocardiograph is indicative of the cyclic motion associated with the heart. Accordingly, the electrocardiograph was used to generate commands for the control of an imaging scanner to produce images of the heart in accordance with the present invention. Specifically, the R-wave of the electrocardiograph is used as a trigger for initiating data acquisition.

The situation wherein a single image slice of a selected phase is desired is depicted in FIGS. 11 and 12. FIG. 11 relates to the situation wherein $T_g = T_c - t_x$ and $n_c$=2.5. The apparatus is turned on and the first R-wave of the electrocardiograph measured is used for timing the data acquisition. The first data acquisition period commences at a time ($t_0$) which occurs at a period of time equal to $\alpha T_c$ after the peak of the first R-wave. Exposure to radiation and data acquisition are initiated at $t_0, t_0+T_c, \ldots, t_0+n_i T_c$. For the first $t_0+(n_i-1)T_c$ data acquisition periods, the radiation remains turned on for a period of time equal to $t_x$. For the last data acquisition period, the radiation remains turned on for a time period of only $n_f t_x$. Accordingly, the total time required to collect a complete set of data for an image slice (i.e., $t_e - t_0$) is $(n_i T_c) + (n_f t_x)$ and the patient is exposed to radiation for a period of time equal to $n_c t_x$.

FIG. 12 depicts the situation wherein $T_g = T_c + t_x$ and $n_c$=3.4. The apparatus is turned on and the first R-wave of the electrocardiograph measured is used for timing the data acquisition. The first data acquisition period commences at a time ($t_0$) which occurs at a period of time equal to $\alpha T_c$ after the peak of the first R-wave. Exposure to radiation and data acquisition are initiated at $t_0, t_0+T_c, \ldots, t_0+(n_i-1)T_c$ and at $t_0+n_i T_c+(1-n_f)t_x$. For the first $t_0+(n_i-1)T_c$ data acquisition periods, the radiation remains turned on for a period of time equal to $t_x$. For the last data acquisition period, the radiation remains turned on for a time period of only $n_f t_x$. Accordingly, the total data acquisition time for an image slice (i.e., $t_e - t_0$) is $n_i T_c + t_x$ and the patient is exposed to radiation for a period of time equal to $n_c t_x$.

Figure 13:
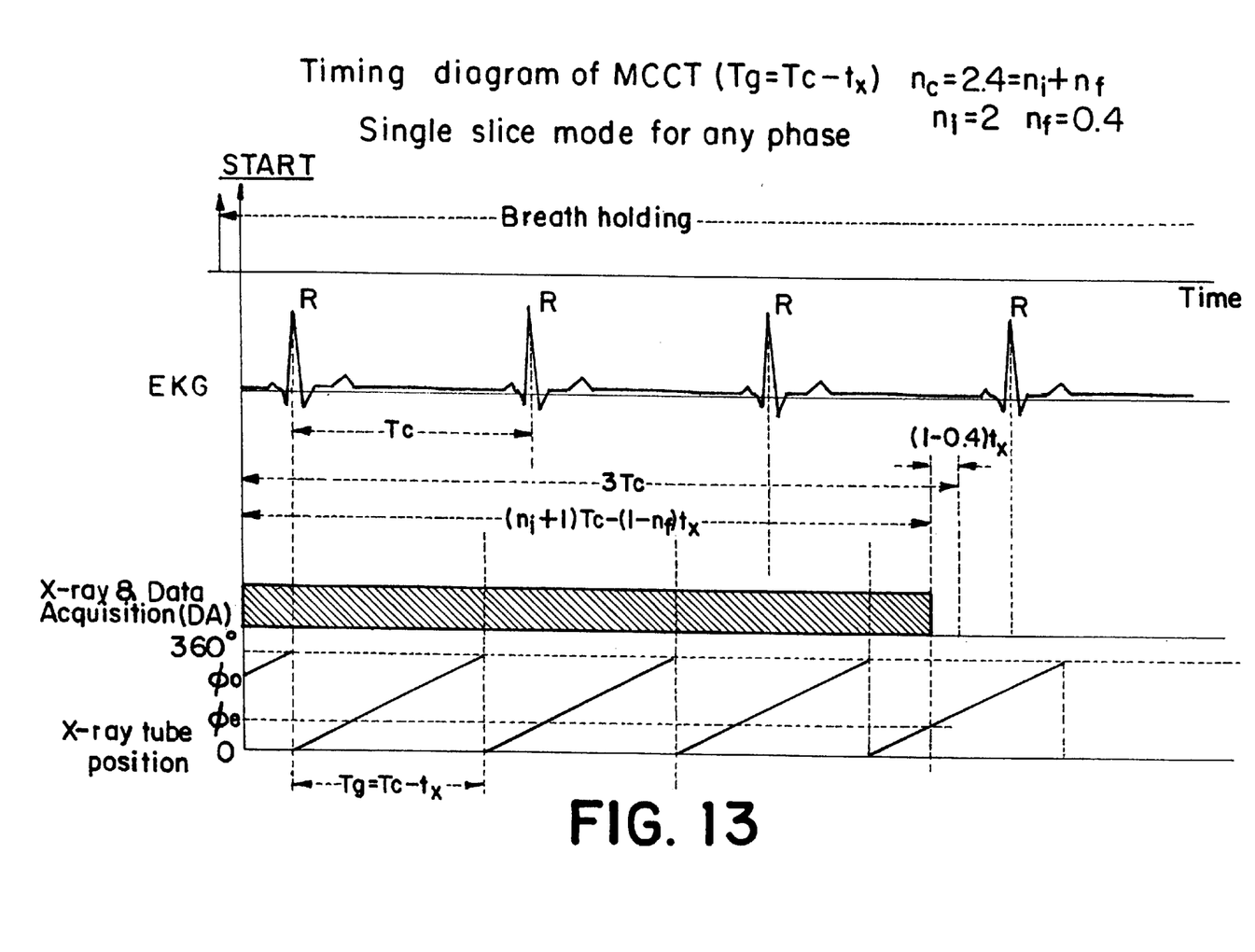
FIG. 13 is a schematic view of a timing diagram for generating a single image slice through a selected object at any phase when the gantry rotation period is the difference between the average period and the window width.
Figure 14:
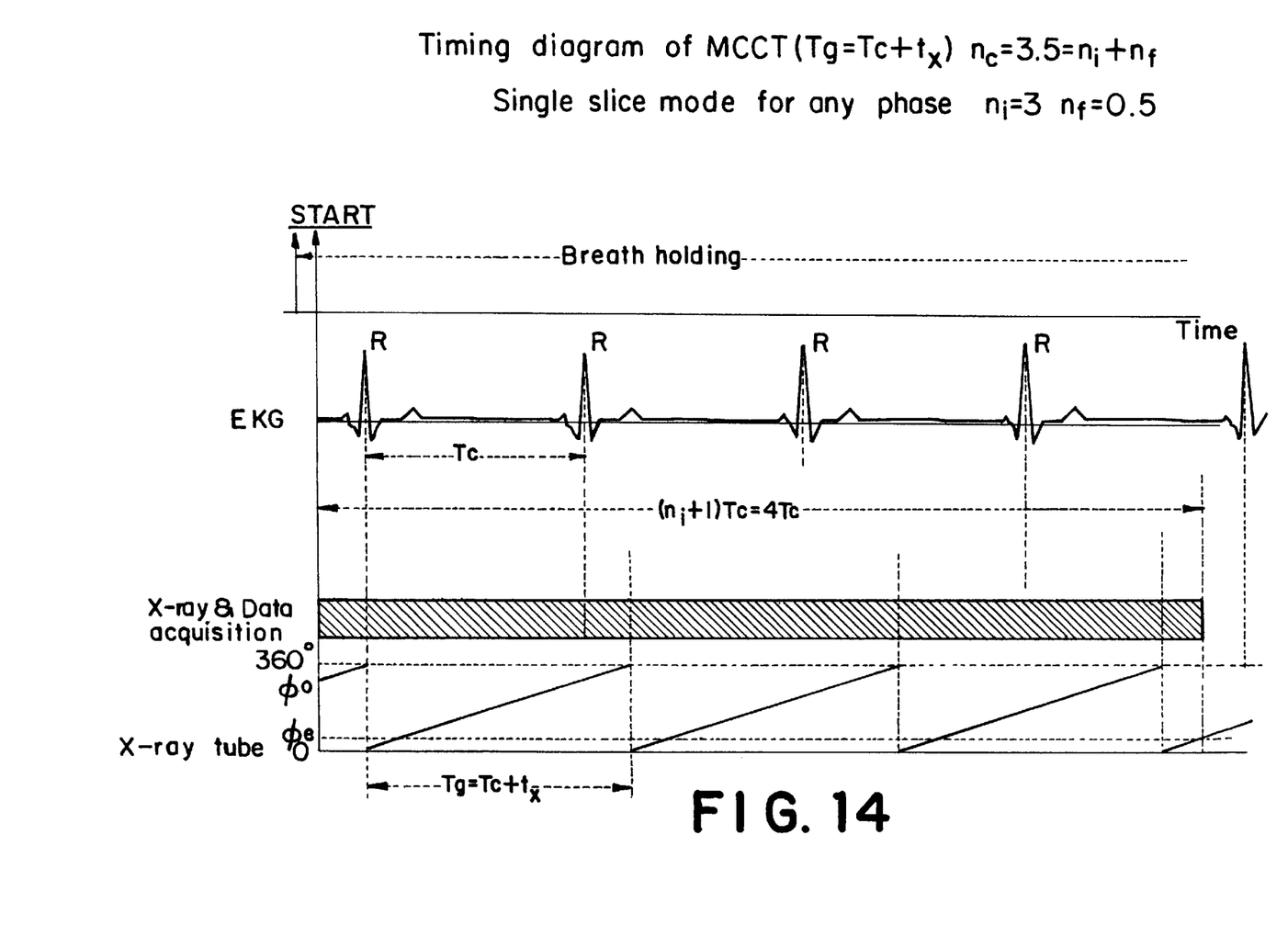
FIG. 14 is a schematic view of a timing diagram for generating a single image slice through a selected object at any phase when the gantry rotation period is the sum of the average period and the window width.

The situation wherein a single image slice of any phase is desired is depicted in FIGS. 13 and 14. The exposure and data acquisition are continuous and may start at any time. The total time span of exposure and data acquisition are $(n_i+1)T_c-(1-n_f)t_x$ for $T_g<T_c$ (FIG. 13) and $(n_i+1)T_c$ for $T_g>T_c$ (FIG. 14).

Figure 15:
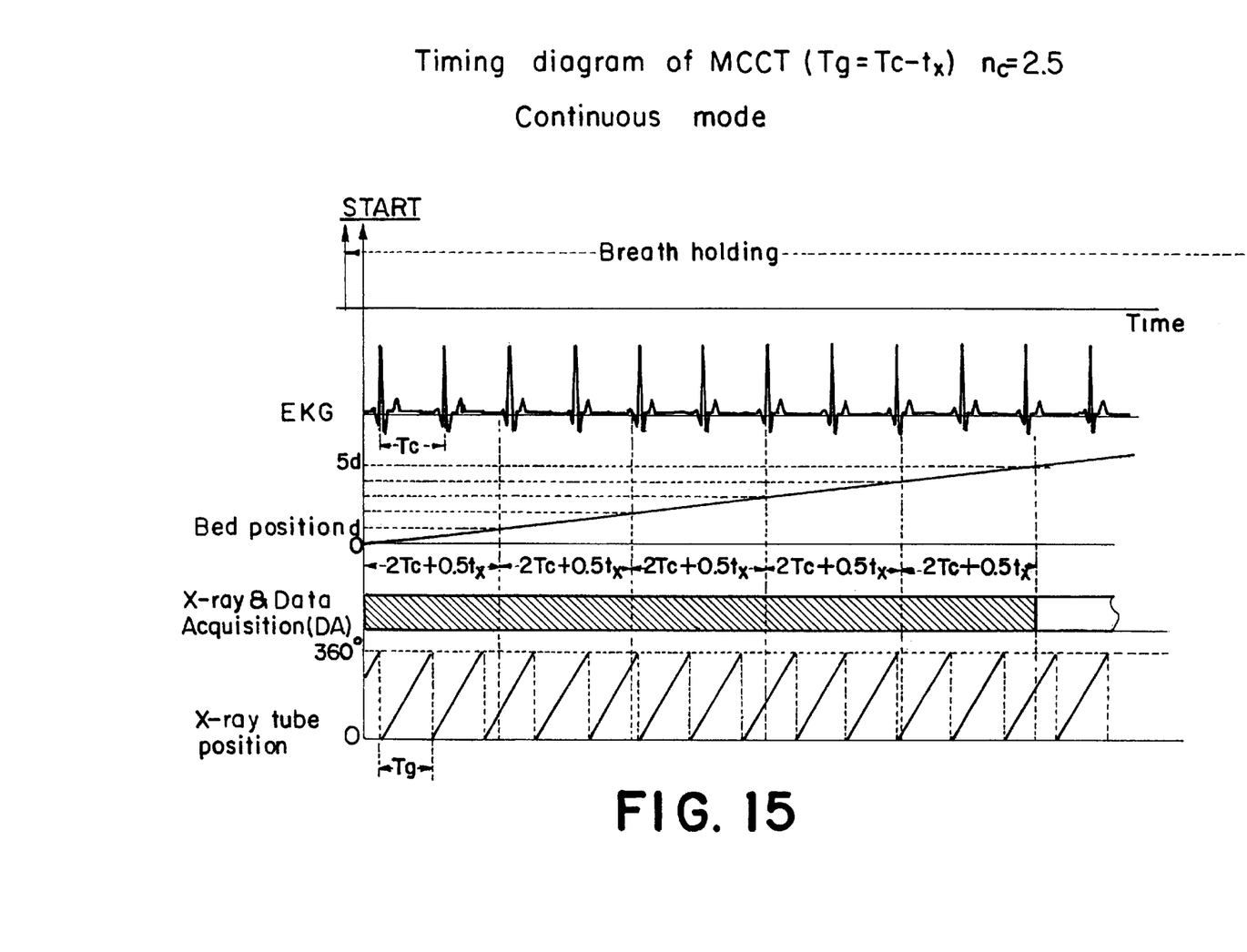
FIG. 15 is a schematic view of a timing diagram for generating a series of image slices through a selected object when the gantry rotation period is the difference between the average period and the window width.
Figure 16:
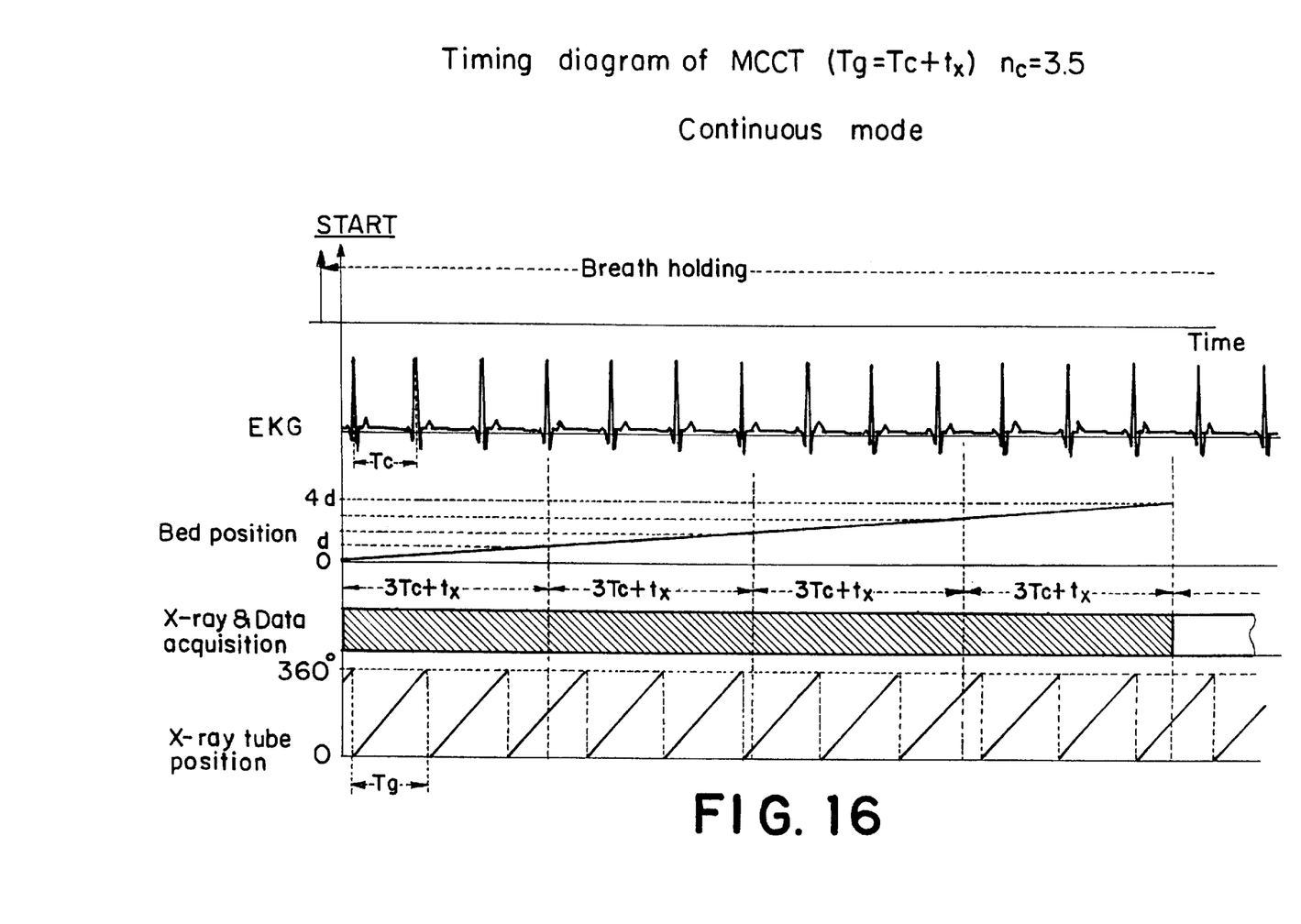
FIG. 16 is a schematic view of a timing diagram for generating a series of image slices through a selected object when the gantry rotation period is the sum of the average period and the window width.

The situation wherein a continuous series of image slices is desired is depicted in FIGS. 15 and 16. The exposure and data acquisition are continuous and may start at any time. However, the bed must move at a matched speed, $V_b$. To determine the bed speed the slice-thickness, d, has to be selected. The bed speed is then determined as the slice-thickness divided by the slice time, $T_b$, wherein $T_b$ equals $n_iT_c+n_ft_x$ for $T_g<T_c$ (FIG. 15) and $n_iT_c+t_x$ for $T_g>T_c$ (FIG. 16).

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for constructing image slices through a selected object undergoing a cyclic motion comprising:
   a. a scanner for collecting image data associated with the selected object;
   b. a probe for detecting a signal from the selected object, the signal being indicative of the cyclic motion; and
   c. a controller operatively connected with the scanner and the probe, the controller adapted to:
      receive the signal from the probe,
      generate an average period of the cyclic motion from the signal,
      select a window width less than the average period of the cyclic motion,
      determine a selected number of cyclic motion periods to obtain a complete set of data from the average period of the cyclic motion and the window width, and
      generate from the selected number of cyclic motion periods a command for enabling the scanner to collect image data for producing the image slice through the selected object at a selected phase of the cyclic motion.

2. The apparatus of claim 1 wherein the controller is adapted to command the scanner to collect the image data at a predetermined phase of the cyclic motion of the selected object.

3. The apparatus of claim 1 wherein the scanner comprises:
   a. a radiation source for irradiating the selected object;
   b. a detector for detecting radiation from the radiation source; and
   c. a gantry having a continuously controllable speed for rotating the radiation source and detector with respect to the selected object.

4. The apparatus of claim 3 wherein the radiation source comprises a plurality of individual radiation sources.

5. The apparatus of claim 3 wherein the detector comprises a one dimensional detector.

6. The apparatus of claim 3 wherein the detector comprises a two dimensional detector.

7. The apparatus of claim 3 wherein the detector comprises a detector disposed in fixed relation to a longitudinal axis of the selected object.

8. The apparatus of claim 3 wherein the scanner further comprises a bed having a continuously controllable speed for supporting the selected object and translating the selected object in a selected direction.

9. The apparatus of claim 8 wherein the controller is adapted to command the scanner to optimize the speed of the bed.

10. The apparatus of claim 3 wherein the controller is adapted to command the scanner to optimize the speed of the gantry.

11. The apparatus of claim 3 wherein the selected object comprises a heart and the probe comprises an electrocardiograph.

12. The apparatus of claim 3 wherein the controller is adapted to generate a gantry rotation period from the average period of the cyclic motion and the window width, and to generate a sampling period from the gantry rotation period and a number of source beams in a complete gantry rotation.

13. The apparatus of claim 1 further comprising an image reconstructing unit.

14. The apparatus of claim 13 wherein the image reconstructing unit comprises:
   a. a reordering unit for generating reordered image data by reordering the image data in an order appropriate for image reconstruction;
   b. a rebinning unit for generating parallel beam data from the reordered image data; and
   c. an image slice reconstructing unit for constructing an image slice of a selected phase of the selected object from the parallel beam data.

15. The apparatus of claim 1 wherein the selected number of cyclic motion periods comprises a minimum number of cyclic motion periods.

16. The apparatus of claim 15 wherein the selected number of cyclic motion periods comprises a minimum number of cyclic motion periods and wherein the controller is adapted to determine the minimum number of cyclic motion periods from the gantry rotation period.

17. The apparatus of claim 1 wherein the scanner comprises:
   a. a radiation source for irradiating the object;
   b. a detector for detecting radiation from the radiation source; and
   c. a gantry having a continuously controllable speed for rotating the radiation source and detector with respect to the object.

18. An apparatus for constructing image slices through a heart undergoing a cardiac motion comprising:
   a. a scanner for collecting image data associated with the heart;
   b. a probe for detecting a signal from the heart, the signal being indicative of the cardiac motion; and
   c. a controller operatively connected to the scanner and to the probe, the controller adapted to:
      receive the signal from the probe,
      generate an average period of the cardiac motion from the signal,
      select a window width less than the average period of the cardiac motion, and
      determine a selected number of cardiac motion periods to obtain a complete set of data from the average period of the cardiac motion and the window width,
      and generating from the selected number of cardiac motion periods a command for enabling the scanner to collect image data for producing the image slice through the heart at a selected phase of the cardiac motion.

19. The apparatus of claim 18 wherein the scanner comprises:
   a. a radiation source for irradiating the heart;
   b. a detector for detecting radiation from the radiation source; and c. a gantry having a continuously controllable speed for rotating the radiation source and detector with respect to the heart.

20. The apparatus of claim 19 wherein the controller is adapted to generate a gantry rotation period from the average period of the cardiac motion and the window width, and to generate a sampling period from the gantry rotation period and a number of source beams in a complete gantry rotation.

21. The apparatus of claim 20 wherein the selected number of cardiac motion periods comprises a minimum number of cardiac motion periods and wherein the controller is adapted to determine the minimum number of cardiac motion periods from the gantry rotation period.

22. The apparatus of claim 18 wherein the selected number of cardiac motion periods comprises a minimum number of cardiac motion periods.

23. A method for constructing at least one image slice through a selected object undergoing a cyclic motion comprising the steps of:
   a. generating an average period of the cyclic motion from a signal derived from the selected object, the signal being indicative of the cyclic motion;
   b. selecting a window width, the window width being less than the average period of the cyclic motion;
   c. generating a gantry rotation period from the average period of the cyclic motion and the window width;
   d. determining a minimum number of cyclic motion periods required to obtain a complete set of data from the average period of the cyclic motion, the window width, and the gantry rotation period;
   e. generating a sampling period from the gantry rotation period and a number of source beams in a complete gantry rotation;
   f. collecting image data associated with the selected object; and
   g. reconstructing the image data to generate an image slice of the selected object.

24. The method of claim 23 further comprising the step of generating a time delay for a selected phase condition from the average period.

25. The method of claim 24 wherein the step of generating the time delay comprises the steps of:
   a. selecting a delay factor; and
   b. determining the time delay as the product of the delay factor and the average period.

26. The method of claim 24 wherein the step of collecting image data comprises the step of transmitting the time delay to a scanner.

27. The method of claim 23 further comprising the step of determining a bed advance speed from the average period, the gantry rotation period, and the minimum number of cyclic motion periods.

28. The method of claim 27 wherein the step of determining the bed advance speed comprises the steps of:
   a. determining a slice time, corresponding to the time required for the bed to move a preselected distance, from the minimum number of cyclic motion periods, the window width, and the average period; and
   b. determining the bed advance speed from the preselected distance and the slice time.

29. The method of claim 27 wherein the step of collecting image data comprises the step of transmitting the bed advance speed to a scanner.

30. The method of claim 23 wherein the step of collecting image data comprises the step of transmitting the gantry rotation speed to a scanner.

31. The method of claim 23 further comprising the step of recording image data associated with the selected object.

32. The method of claim 23 wherein the step of reconstructing the image data comprises the steps of:
   a. reordering the image data to generate reordered image data, the reordered image data being in an order appropriate for image reconstruction;
   b. rebinning the reordered image data to generate parallel beam data; and
   c. constructing an image slice of a selected phase of the selected object from the parallel beam data.

33. The method of claim 23 wherein the step of generating the average period of the cyclic motion comprises the steps of:
   a. measuring an individual period for each of a preselected number of cyclic motions;
   b. determining an average period from the individual periods;
   c. determining a standard deviation associated with the average period;
   d. storing the average period if the average period is less than the threshold value; and
   e. measuring a new period and returning to step b if the average period is not less than the threshold value.

34. The method of claim 23 wherein the step of selecting the window width comprises the step of determining the window width from the average period.

35. The method of claim 23 wherein the step of generating the gantry rotation period comprises the steps of:
   a. comparing a difference between the average period and the window width with a minimal gantry rotation period;
   b. setting the gantry rotation period to the difference between the average period and the window width if the difference is not less than the minimal rotation period; and
   c. setting the gantry rotation period to the sum of the average period and the window width if the difference is less than the minimal rotation period.

36. The method of claim 23 wherein the step of generating the minimum number of cyclic motion periods comprises the steps of:
   a. selecting a field of view based on the size of the object being imaged;
   b. determining a full fan angle, $\phi_f$, from the field of view; and
   c. generating the minimum number of cyclic motion periods as $$n_c = \frac{(180° + \phi_f)}{360°} \frac{T_g}{t_x},$$

wherein $T_g$ represents the gantry rotation period and $t_x$ represents the window width.

* * * * *